United States Patent [19]
Thornburg

[11] Patent Number: 5,939,288
[45] Date of Patent: Aug. 17, 1999

[54] PLANT SECRETORY SIGNAL PEPTIDES AND NECTARINS

[75] Inventor: Robert Thornburg, Ames, Iowa

[73] Assignee: Iowa State University Research Foundation, Inc., Ames, Iowa

[21] Appl. No.: 08/478,259

[22] Filed: Jun. 7, 1995

[51] Int. Cl.[6] ............................ C12N 15/29; C12N 15/62; C12N 15/82; C12N 5/04; A01H 5/00
[52] U.S. Cl. ................... 435/69.8; 435/69.4; 435/69.51; 435/69.52; 435/69.6; 435/69.7; 435/70.1; 435/193; 435/197; 435/199; 435/200; 435/219; 435/411; 435/412; 435/415; 435/414; 435/417; 435/419; 435/468; 435/320.1; 536/23.4; 536/23.6; 800/278; 800/282; 800/288; 800/298
[58] Field of Search ................................ 435/69.1, 69.7, 435/69.8, 70.1, 172.3, 240.4, 320.1, 419, 468, 69.4, 69.51, 69.52, 69.6, 193, 197, 199, 200, 219, 411, 412, 415, 414, 417; 800/205, 278, 282, 288, 298, 305–307, 311–315, 317.2–317.4, 320–320.3, 321, 319, 323.2–323.3; 536/23.2, 23.4, 23.6

[56] References Cited

U.S. PATENT DOCUMENTS

| | | | |
|---|---|---|---|
| 5,164,316 | 11/1992 | McPherson et al. | 435/240.4 |
| 5,175,095 | 12/1992 | Martineau et al. | 435/69.1 |
| 5,234,834 | 8/1993 | Fischer et al. | 435/320.1 |
| 5,349,122 | 9/1994 | Hain et al. | 800/205 |

OTHER PUBLICATIONS

B.D. Davis & P.C. Tai, "The Mechanism of Protein Secretion Across Membranes" *Nature* 283: 433–438 (1980).

J. Huang et al. "A Yeast Mitochondrial Leader Peptide Functions In Vivo as a Dual Targeting Signal for Both Chloroplasts and Mitochondria" *The Plant Cell.* 2: 1249–1260 (1990).

B.G. Lane et al., "Germin, a Protein Marker of Early Plant Development, is an Oxalate Oxidase" *J. Biol. Chem.* 268: 12239–12242 (1993).

S.G. Rogers et al., "Gene Transfer in Plants: Production of Transformed Plants Using Ti Plasmid Vectors" *Meth. Enzymol.*, 118: 627–640 (1986).

D. Santosa & R.W. Thornburg., "Isolation and Characterization of UMP Synthase Mutants from Haploid Cell Suspensions of *Nicotiana tabacum*" *Plant Physiol.* 99: 1216–1225 (1992).

M.R. Schroeder et al., "Colocalization of Barley Lectin and Sporamin in Vacuoles of Transgenic Tobacco Plants" *Plant Physiol.* 101: 451–458 (1993).

N.Q. Shi & R. Thornburg, "Construction of a UMP Synthase Expression Cassette from *Dictyostelium discoideum*" *Gene* 127: 199–202 (1993).

M.W. Shieh et al., "Nuclear Targeting of the Maize R Protein Requires Two Nuclear Localization Sequences" *Plant Physiol.* 101: 353–361 (1993).

Tang et al. 1994. Plant Cell 6(9):1227–1239.

Thoma et al. 1994. Plant Physiol. 105(1):35–45.

Hippe et al. 1989. Eur. J. Cell Biol. 50:230–234.

*Primary Examiner*—David T. Fox
*Attorney, Agent, or Firm*—Baker & Botts, LLP

[57] ABSTRACT

Provided herein are signal peptides, and constructs and vectors having signal peptides, as well as methods of using signal peptides to deliver proteins into secretory material. The invention facilitates the purification of recombinant proteins. Also provided are a new class of proteins called nectarins, from which the signal peptides may be derived. Additionally, the nectarins possess oxalate oxidase activity and have utility as agents for treating diseases or conditions relating to abnormal oxalate deposition or metabolism or as diagnostics for measuring oxalate concentrations in specimens.

48 Claims, 3 Drawing Sheets

Figure 1.

(Nec) DEDMLQDVCVADLHSK VKVNGPPCK
(HvG) MGYSKTLAVSLFAVLLLAPAVLASDPDPLQDFCVADLDGKAVSVNGHPCKPMSE
(WGA) MGYSKTLVAGLFAMLLLAPAVLATDPLQDFCVADLDGKAVSVNGHTCKPMSE
(BG)   SDPDPLQDFCVADLDGKAVSVNGHTCKPMSE

PLANT SECRETORY SIGNAL PEPTIDES AND NECTARINS

BACKGROUND OF THE INVENTION

1. Field of the Invention

The present invention relates to purified signal peptides for use in facilitating secretion of one or more proteins from plant cells. The present invention also relates to nectarins, proteins derived from nectar which possess oxalate oxidase activity. The present invention also relates to methods for treating diseases or conditions related to abnormal oxalate deposition.

2. Description of the Background

Genetically engineered proteins are expressed in two ways: via intracellular expression and via secreted expression. In intracellular expression, host cells are isolated and homogenized to form an extract from which expressed proteins are purified. Extract production involves mechanical disruption of the host cells, followed by extraction of soluble proteins. The ease of host cell extraction varies by cell type. Animal cells can easily be homogenized with a hand homogenizer, but yeast and bacteria require vigorous mechanical treatment. Plant cells are particularly difficult to disrupt because they have durable cell walls. Also, plant cells have subcellular organelles containing compounds such as proteases, polyphenols, and alkaloids which, upon disruption, rapidly degrade and inactivate proteins. Furthermore, cell extracts may comprise over one thousand (1000) different species of proteins. Depending on the intended use of the expressed proteins, substantial effort may be required for their isolation and purification from such complex environments.

Secreted expression, on the other hand, lacks many of these drawbacks. Secreted proteins are easier to purify because the extracellular environment into which proteins are secreted, has few, if any, contaminating proteins. With the attachment of a signal peptide, a host cell can be directed to secrete most proteins of interest.

In the natural state, signal peptides guide proteins from their synthesis site to their functional location. Secretory signal peptides guide proteins outside the cell, and are typically about fifteen to about sixty amino acids long. After a protein is properly transported, the signal peptide is removed and has no further effect on the function of the mature protein.

The mechanism of protein secretion has been reviewed by Davis and Tai, *Nature* 283, 433–438 (1980). In all species, the exact amino acid sequence of the signal peptide appears to be less important than the physical properties of the amino acids that constitute the peptide. For example, an acidic amino acid may be replaced with another acidic amino acid without impairing signal peptide function.

Plants, like other organisms, utilize signal sequences to direct protein transport. These signal sequences, like their mammalian counterparts, are interchangeable and functionally independent of the attached protein. Shieh et al., *Plant Physiol.* 101, 353–361 (1993). When proteins non-native or foreign to a plant cell are attached to a signal peptide, they are transported and processed in a similar fashion to endogenous or native plant cell proteins.

Few systems have been developed for the production of secreted proteins. *E. coli* usually does not produce secreted proteins because of its simplicity, and yeasts secrete only small proteins. While mammalian cells readily secrete proteins, the secreted proteins are difficult to purify because they are often expressed at low levels. Plant secretory signal peptides are known to exist because some plant proteins are known to occur extracellularly. However, plant secretory peptides have heretofor not been isolated. Consequently, methods using signal peptides for secreted expression of proteins from plants have not been developed.

Plants and plant cells have unique advantages as host organisms for protein production. Plant cultivation and plant cell culture is less demanding than mammalian cell culture. A number of attributes of plants and plant cells contribute to their low maintenance cost. For example, plants and plant cells do not require expensive media and do not generate liquid biohazardous waste. The ability of plants and plant cells to grow in a wide range of temperature, humidity, and oxygen levels also contributes to their low maintenance cost. Additionally, proteins produced from bacteria or other micro-organisms are not adequately glycosylated. In contrast, plants and plant cells glycosylate proteins using the same molecular machinery as animals.

Consequently, there is a strong need for a method which provides for protein secretion into plant secretory materials. The ability to isolate and purify proteins from plant secretory materials would allow an efficient and cost-effective means of using plants to express recombinant proteins.

Disclosed herein are proteins identified in the secretory material of plant nectar. The proteins, called nectarins, are secreted via mechanisms which utilize signal peptides. As will become apparent from the following detailed description, these and other signal peptides can be used to transport recombinant proteins into secretory material. Furthermore, it has been discovered that the nectarins possess oxalate oxidase activity. The importance of this finding will now be addressed.

Diseases or conditions associated with abnormal deposition or regulation of oxalate take a strong clinical toll. For example, urolithiasis (kidney stones) is responsible for seven to ten of every one thousand hospital admissions in the United States. Also, disorders such as hereditary primary oxaluria and secondary oxaluria associated with enteric disease leads to abnormal deposition of oxalate. The most popular method for treating kidney stones is lithotripsy. However, this method is dependent upon identification of stones after they have already been formed. Diet is often manipulated to reduce the risk of developing kidney stones. About 75% of stones are composed of calcium oxalate or calcium oxalate mixed with calcium phosphate. A pharmaceutical agent possessing the ability to catalyze the degradation of oxalate would therefore have significant clinical utility for treating diseases or conditions related to abnormal deposition of oxalate. Additionally, methods for determining oxalate concentrations in fluids and biological specimens often utilize coupled enzymatic reacting employing oxalate oxidase. Proteins possessing oxalate oxidase activity therefore have utility in these and other detection methods.

SUMMARY OF THE INVENTION

It is an object of the present invention to provide methods for purifying proteins from plant secretory material. It is also an object of the present invention to provide plant protein secretory signal sequences and novel methods of expressing one or more proteins in plants. It is also an object of the present invention to provide a method for catalyzing the degradation of oxalate into carbon dioxide and hydrogen peroxide. It is also an object of the present invention to provide a method of treating diseases and conditions related to abnormal deposition of oxalate.

Accordingly, the present invention provides a method for expressing protein into secretory material comprising introducing into a plant cell a nucleic acid construct comprising DNA that encodes a signal peptide and at least one protein, wherein said signal peptide facilitates secretion of said at least one protein from said plant cell into said secretory material. Also provided in the present invention are purified signal peptides comprising a peptide having an amino acid sequence that facilitates secretion of a protein from a plant into secretory material.

The present invention also provides purified nucleic acid constructs comprising DNA that encodes a signal peptide and at least one protein, wherein said signal peptide facilitates secretion of said at least one protein from said plant into secretory material. Also provided are recombinant vectors comprising DNA that encodes a signal peptide and at least one protein, wherein said signal peptide facilitates secretion of said at least one protein from a plant into secretory material.

Furthermore, the present invention provides recombinant plants or recombinant plant cells comprising a nucleic acid construct comprising DNA that encodes a signal sequence and at least one protein, wherein said signal sequence facilitates extracellular secretion of said at least one protein from a plant or a plant cell.

Also provided in the present invention is a method for quantitating expression of a non-native protein in secretory material comprising the steps of creating a first nucleic acid construct that encodes a signal peptide sequence and a protein, wherein said signal peptide sequence facilitates secretion of a protein from a plant cell into secretory material, creating a second nucleic acid construct that encodes a signal peptide sequence and a detecting enzyme sequence, wherein said signal peptide sequence facilitates secretion of a detecting enzyme into secretory material, introducing said first construct and said second construct into a plant cell and culturing said plant cell for a sufficient time to secrete said protein and said detecting enzyme, contacting a substrate or a substrate analog for said enzyme with the secretory material, and detecting the reaction product of said detecting enzyme and said substrate.

In an alternate embodiment of the present invention is provided a method for treating diseases or conditions related to deposition of oxalate in an animal comprising administering an effective amount of a nectarin to said animal in need of treatment. Also provided is a method for catalyzing the cleavage of oxalate in a specimen comprising subjecting said specimen to an effective amount of a nectarin to cleave said oxalate into hydrogen peroxide and carbon dioxide and detecting the amount of said hydrogen peroxide or carbon dioxide generated.

Furthermore, the present invention provides for purified and isolated Nectarin I, Nectarin II, Nectarin III, and Nectarin IV.

Other embodiments and advantages of the invention are set forth, in part, in the description which follows and, in part, will be obvious from this description or may be learned from the practice of the invention.

DETAILED DESCRIPTION OF THE INVENTION

The present invention is directed in part to signal peptides which cause the extracellular secretion of proteins from plants and/or plant cells. The signal peptides of the present invention may be used in any suitable plant, plant cell and/or plant cell culture that produces extracellular secretions into secretory material. "Secretory material" as defined in the present invention includes, but is not limited to, nectar, saline, mineral solutions, mucilage, digestive solutions, lipophilic substances, sap, latexes and cell culture media. Preferably, the secretory material chosen will have low concentrations of proteins which might hinder recombinant protein purification. For example, nectar from tobacco plants naturally has only four distinct proteins, which are generally herein identified as nectarins. More specifically, the nectarins are Nectarin I, II, III, and IV. Accordingly, nectar provides an excellent secretory material for protein collection. Similarly, plant cell culture media typically have no or negligible protein content. Suitable media include, but are not limited to 8p, 6p, BSH, $B_3$, DPD, E1 media (E1), F5, Gamborg's B5 media (B5), Green, Kao #3, Lam, Linsmaier and Skoog media (LS), Medium A, Medium B, Murashigbe and Skoog media (MS), N6 media (N6), NT, Nitsch & Nitsch, Nitsch, Ohyama, Schenk and Hildebrandt media, $T_0$, Upadyha, V-KM, V47, White's media (WH), and Z.

Most plant species have the capability of secreting proteins into secretory material and may be used in the present invention, both as host cells and as sources of signal peptides. Suitable plant species include, but are not limited to, any of the several species from among the following genera: Agave, Albizzia, Allium, Aloe, Ammi, Amoracia, Anagallis, Ananas, Andropogon, Anethum, Anthurium, Antirrhinum, Apium, Arabidopsis, Arachis, Asparagus, Atropa, Avena, Averrhoa, Begonia, Beta, Betula, Biota, Brachycome, Brassica, Bromus, Broussonetia, Browallia, Cajanus, Capsicum, Carica, Carum, Caucus, Centaurea, Ceratonia, Cheiranthus, Chrysanthemum, Cichorium, Citrus, Crotalaria, Coffea, Consolida, Convolvulus, Coptis, Conium, Cordyline, Coriandrum, Corylus, Crambe, Crassula, Crepis, Cupressus, Cucurbita, Cynara, Cyclamen, Dactylis, Datura, Daucus, Digitalis, Dioscorea, Diospyros, Dracaena, Drimys, Elaeis, Eleusine, Eschscholzia, Euphorbia, Fagopyrum, Festuca, Foeniculum, Gazania, Glycine, Gossypium, Haworthia, Hedera, Heloniopsis, Hemerocallis, Hordeum, Hyacinthus, Hyoscyamus, Iberis, Ilex, Indigofera, Ipomea, Iris, Lactuca, Lathyrus, Lilium, Limnophyla, Linum, Liquidambar, Lobularia, Lolium, Lotus, Lycopersicon, Macleaya, Malus, Mammillaria, Manihot, Mazus, Medicago, Mesembryanthemum, Muscari, Narcissus, Nemesia, Nicotiana, Nigella, Ornithogalum, Oryza, Panicum, Panox, Papaver, Parthenium, Parthenocissus, Paspalum, Passiflora, Paulownia, Pelargonium, Pennisetum, Peperomia, Pergularia, Perilla, Petraniva, Petroselium, Petunia, Phaseolus, Phoenix, Phlox, Phragmites, Physalis, Picea, Pimpinella, Pinus, Pisium, Populus, Prunus, Pseudotsuga, Psophocarpus, Pterotheca, Ranunculus, Rosa, Rubus, Saccharum, Salpiglossis, Santalum, Scopalia, Scilla, Sedum, Senecio, Sinapis, Sisymbrium, Sium, Solanum, Sorghastrum, Sorghum, Stevia, Stylosanthes, Taraxacum, Thalictrum, Theobroma, Tylophora, Thuja, Torenia, Trifolium, Trigonella, Triticale, Triticum, Ulmus, Verbascum, Vicia, Vigna, Vitis, Zea, and Zingiber. Preferably, the plants are Nicotiana species.

In a preferred embodiment, the present invention is directed to signal peptides which cause the secretion of proteins into secretory material. A signal peptide may be identified by comparing the primary amino acid sequence of the full-length and mature secreted protein forms exclusive of any pro-piece necessary for protein storage or packaging. Standard amino acid sequencing techniques may be used. The difference between the two primary amino acid sequences is the signal peptide sequence. Amino acid sequences, derived from protein sequencing of purified secreted plant protein and full-length pre-protein are compared to determine the signal peptide sequence.

Suitable secreted plant proteins from which signal peptides may be derived include, but are not limited to, nectarins, papain, protease, acid phosphatase, esterase, ribonuclease, peptidases, digestive enzymes, and extensins. In a preferred embodiment, the amino acid sequences, derived from protein sequencing of a purified Nectarin I and pre-Nectarin I are compared to determine the sequence of the Nectarin I signal peptide. In one embodiment of the present invention, the Nectarin I signal peptide is used to direct proteins for secretion into nectar. In another embodiment, the Nectarin I signal peptide is used to direct proteins for secretion into cell culture media. It will be appreciated that signal peptides from Nectarin II, III and IV can be identified in a similar fashion and can also be used to direct proteins for secretion into secretory material.

The signal peptides of the present invention are usually between five to two hundred amino acids in length, preferably about ten to one hundred amino acids in length, and most preferably about fifteen to sixty amino acids in length. The function of a signal peptide is generally unaltered by the replacement of one amino acid with another amino acid from the same functional group. One or more of the amino acids of the secretory signal peptide of the present invention can be substituted by at least one different amino acid from the same functional group. As used herein, the different "functional groups" are: (1) non-polar amino acids, (2) polar neutral amino acids, (3) positively charged amino acids, and (4) negatively charged amino acids. Amino acids having similar characteristics are listed in the following groups. The non-polar amino acids are alanine, leucine, isoleucine, valine, proline, phenylalanine, tryptophan, and methionine. The polar neutral amino acids are glycine, serine, threonine, cysteine, tyrosine, asparagine, and glutamine. The positively charged amino acids are arginine, lysine, and histidine. The negatively charged amino acids are aspartic acid and glutamic acid.

In an alternative embodiment of the present invention, the DNA encoding the protein to be expressed may be ligated with DNA encoding a signal peptide to create a fusion gene. Preferably, gene fusion will not affect the ultimate form of the protein to be expressed, as the signal peptide is removed from the fusion protein during or after secretion into the secretory material. Due to the degeneracy of nucleotide coding sequence, DNA sequences which encode substantially the same amino acid sequence as the signal peptide may also be used in the practice of this invention.

The choice of the particular gene(s) to be delivered to the plant will often depend on the purpose of the transformation. Gene(s) coding for protein(s) non-native (i.e., foreign) to the plant, and gene(s) coding for protein(s) native to the plant, and combinations thereof may be employed in the present invention. As used herein, "protein" refers to polypeptide or protein. This includes the production of important proteins or other products for commercial use, such as, but not limited to, lipase, melanin, pigments, antibodies, hormones, growth factors, amylase, protease, L-asparaginases, rennin, lipase, proteinase inhibitor, oxalate oxidase, acylase, pharmaceuticals such as, but not limited to, interleukins, EPO, G-CSF, GM-CSF, hPG-CSF, M-CSF, Factor VIII, Factor IX, TPA, hGH, receptors, insulin, interferon, antithrombin III, trans-cobalamins, glucagon, vaccines, antibiotics and the like. Useful vaccines include, but are not limited to, hepatitis B surface antigen, polio vaccine, HIV vaccine, mumps vaccine, Streptococcal M-protein vaccines, diphtheria toxoid, tetanus toxoid, protective antigens, veterinary vaccines for diseases such as bovine foot and mouth disease, canine distemper and others. The genes may also code for fusion proteins. The coding sequences for proteins that can be used are known in the art or can be obtained by standard sequencing techniques. Alternatively, the method may be used to produce an enzyme that is able to convert a natural product to a unique product. This includes, for example, the production of secondary metabolites useful as pharmaceuticals. Alternatively, the method may be used to alter cellular metabolism leading to altered nutrient or other phenotypic trait(s) of the plant.

In an alternative embodiment, the method is used to transform plants or plant cells to add some commercially desirable, agronomically important traits to the plant or plant cells. Such traits include, but are not limited to, insect and disease resistance, physical appearance, food content, and makeup, etc. For example, one may desire to incorporate one or more genes encoding one or more proteins which confer insecticidal properties. Alternatively, one may desire to incorporate one or more genes encoding one or more proteins which confer enhanced insect nutrition. For example, proteins which are beneficial to honey bees may be expressed in plants and secreted into plant nectar to improve the quality or nutritional value of honey. In some cases, genes encoding proteins native to the plant may be added. These include, but are not limited to, proteinase inhibitor, chitinase, cutinase, cholesterol hydroxylase, SAM-protocatechuate methyl transferase, vanillic acid dehydrogenase, oxalate oxidase, peroxidase, papain, ribonuclease, and protease.

One method for introducing a gene to the plant for extracellular expression is to initially combine the gene with an expression cassette comprising in a 5' to 3' direction: a promoter DNA (constitutive or inducible), a translation initiation sequence, a signal peptide, a multiple cloning site, and a terminator. Optionally, an affinity tag may be added between the signal peptide and the multiple cloning site. It will be appreciated by one of skill in the art that an affinity tag could be placed most easily at the N-terminus and/or at the C-terminus. Internal tags may also be used, but their use is limited by the possibility that they may disable the protein's function. Hence a gene with a restriction site in any of the three reading frames may be ligated in frame and expressed as a fusion protein with the signal peptide and at least one optional affinity tag. In some cases, it will be advantageous to place a plurality of affinity tags on the secreted protein.

In one embodiment of the present invention, an affinity tag may be attached to the expressed protein to facilitate purification. An affinity tag is a protein fragment having specific binding affinity to a chromatography resin. Protein fragments useful as affinity tags include, but are not limited to, polyhistidine, beta-galactosidase, polycysteine, FLAG antigen, biotin and maltose binding protein. For example, fusion proteins which comprise these moieties may be purified by affinity chromatography using nickel resin, FLAG antibody resin, and maltose resin. In one embodiment of the present invention, DNA encoding one or more affinity tags is placed 3' and in frame with the DNA encoding the signal peptide.

If additional purity of the expressed protein is desired, a combination of conventional purification and affinity purification procedures may be used. Additional purification may also be achieved by the attachment of multiple affinity tags. Multiple tags may be placed, for example, at the N-terminus, the C-terminus, or at both the N-terminus and the C-terminus. For example, the poly-histidine and the FLAG tag are useful in combination because they can function when juxtaposed. The affinity tagged protein may comprise an amino acid sequence to allow removal of the affinity tag following enteropeptidase cleavage. One embodiment of this invention is directed to the use of enteropeptidase cleavage site of Val-Asp-Asp-Asp-Asp-Lys. An affinity tag that also contains the enteropeptidase cleavage site can be removed from the expressed protein by enteropeptidase.

To further facilitate the cloning of a non-native gene, a multiple cloning site may be placed 3' of the sequence encoding the plant signal peptide in the expression vector. The site may contain one or more restriction endonuclease cleavage sites along an open reading frame. A set of three cloning vectors, with the multiple cloning site in all three reading frames with respect to the signal peptide is provided so that any open reading frame may be cloned into the expression vector with minimal genetic manipulation.

The purified nucleic acid construct of the present invention may include at least one inducible promoter, one organ specific promoted or one constitutive promoter to facilitate expression. Suitable inducible promoters include, but are not limited to, thermal inducible promoters, metal inducible promoters, wound inducible promoters, hormone inducible promoters, photosensitive inducible promoters, gas inducible promoters, pathogen inducible promoters, stress inducible promoters, and combinations thereof. Suitable organ specific promoters include, but are not limited to, callus specific promoters, fruit specific promoters, tuber specific promoters, root specific promoters, leaf specific promoters, stem specific promoters, and flower specific promoters. Suitable constitutive promoters include but are not limited to 35S or 19S Cauliflower Mosaic Virus promoters, octopaine synthase promoter, nopaline synthase promoter, and actin promoters.

The expression vectors of the present invention may be joined to one or more markers for selection in plant cells. In order to improve the ability to identify transformants, one may desire to employ a selectable and/or screenable marker gene as, or in addition to, the expressible gene of interest. Such genes may encode either a selectable or screenable marker, depending on whether the marker confers a trait which one can select for by chemical means, i.e., through the use of a selective agent such as an herbicide, antibiotic or the like, or whether it is simply a trait that one can identify through observation or testing (e.g., the R-locus trait). Many examples of suitable marker genes are known to the art and can be employed in the practice of the present invention.

Possible selectable markers for use in connections with the present invention include, but are not limited to, thymidine kinase, dihydrofolate reductase, animoglycoside phosphotransferase, hygromycin B phosphotransferase, xanthine-guanine phosphoribosyl transferse, CAD protein, adenosine deaminase, neomycin phosphototransferase, chloramphenicol acetyl transferse, asparagine synthetase, herbicide resistance genes, metallothionine, cytosine deaminase, and combinations thereof. Exemplary screenable markers include beta-glucuronidase (GUS), chloramphenicol acetyl transferase (CAT) or an R-locus gene, which encodes a product that regulates the production of anthocyanin pigments (red color) in host cells.

In another embodiment of the present invention, signal peptide/reporter gene fusions may be used to test for mutagenic potential. For example, the signal peptide/reporter gene could be engineered such that it would not be expressed in cells that contain the engineered fused gene. If the transgenic plant cells were subjected to a mutagen, or if the transgenic plants were grown in soil containing a mutagen, the mutation could restore reporter gene activity. Likewise, inactivation of reporter gene expression could also be used to test for mutagenic activity. Reporter genes which are useful in the present invention include, but are not limited to, β-galactosidase, chloramphenicol acetyl transferase, neomycin phosphotransferase, nopaline synthetase, octopine synthase, firefly luciferase, bacterial luciferase, and combinations thereof.

After the gene is inserted in the expression cassette, plant cell transfection is carried out using known plant transformation techniques. A number of methods well known to those skilled in the art can be used to transform plants with the expression vectors of the present invention. These include, but are not limited to, A. tumefaciens mediated transformation, A. rhizogenes mediated transformation, polyethylene glycol or calcium mediated transformation, electroporation, microinjection, and high velocity particle bombardment. The tissue, organ, seed, cell culture of a plant, and/or the plant itself may be descended from or contain a cell transformed by a construct of this invention.

The present invention also provides for a signal peptide lambda cDNA library. Such a library is screened using the same techniques as other cDNA libraries and which are well known to those skilled in the art. Once a positive clone is identified, the plasmid within the phage DNA can be excised by co-transfection of E. coli or other suitable host cell with the positive phage and the helper phage. The resultant host cells containing the plasmid of interest can be directly used to transform plant cells using standard methods such as, but not limited to, tri-parental culture or direct DNA transformation. Using a signal peptide cDNA library, those of ordinary skill can proceed from positive phage identification to signal peptide plant expression without sequencing and subcloning.

Provided in alternative embodiment of the present invention is a method for quantitating expression of a non-native or a native protein in plant secretory material. The method comprises creating a first nucleic acid construct that encodes a signal peptide sequence and a protein sequence, and creating a second nucleic acid construct that encodes a signal peptide sequence and a detecting enzyme sequence, wherein the signal peptide sequence of the second nucleic acid construct facilitates secretion of a detecting enzyme into secretory material. In this method, the first construct and the second construct are introduced into a plant cell using standard techniques. The recombinant plant cell is grown for a sufficient time to produce and secrete the protein and detecting enzyme. Those skilled in the art will be able to ascertain a sufficient time based on host cell type, culture conditions, expressed proteins of interest, and minimal concentration needed for detection. A substrate or suitable substrate analog for the detecting enzyme is added to the secretory material and the reaction product of the detecting enzyme and the substrate is measured using standard techniques. Suitable detecting enzymes include, but are not limited to, β-galactosidase, chloramphenicol acetyl transferase, neomycin phosphotransferase, nopaline synthetase, octopine synthase, firefly luciferase, bacterial luciferase, and combinations thereof. The detection technique chosen will depend on the detecting enzyme and substrate chosen, as well as on the instrumentation available for detection. Suitable detection techniques include, but are not limited to, visual inspection, coupled enzymatic reactions, thin layer chromatography, photospectrometry, fluorometry, autoradiography, radioactivity detection, and combinations thereof.

In an alternative embodiment of the present invention, Nectarins I, II, III and/or IV, and combinations thereof, are used to treat diseases or conditions related to abnormal deposition of oxalate in an animal. "Animal" refers to a human or an animal. As used herein, the term "nectarin" refers generally to the nectarin proteins isolated from nectar. The N-terminal amino acid sequence of Nectarin I (disclosed in Example 1, below) is closely related to the primary amino acid sequence of Germin, as determined by a BLAST search of Genbank. It is known to those skilled in the art that Germin has oxalate oxidase activity. Oxalate oxidase, (E.C. 1.2.3.4.) catalyses the degradation of oxalate into carbon dioxide and hydrogen peroxide.

Figure 1:
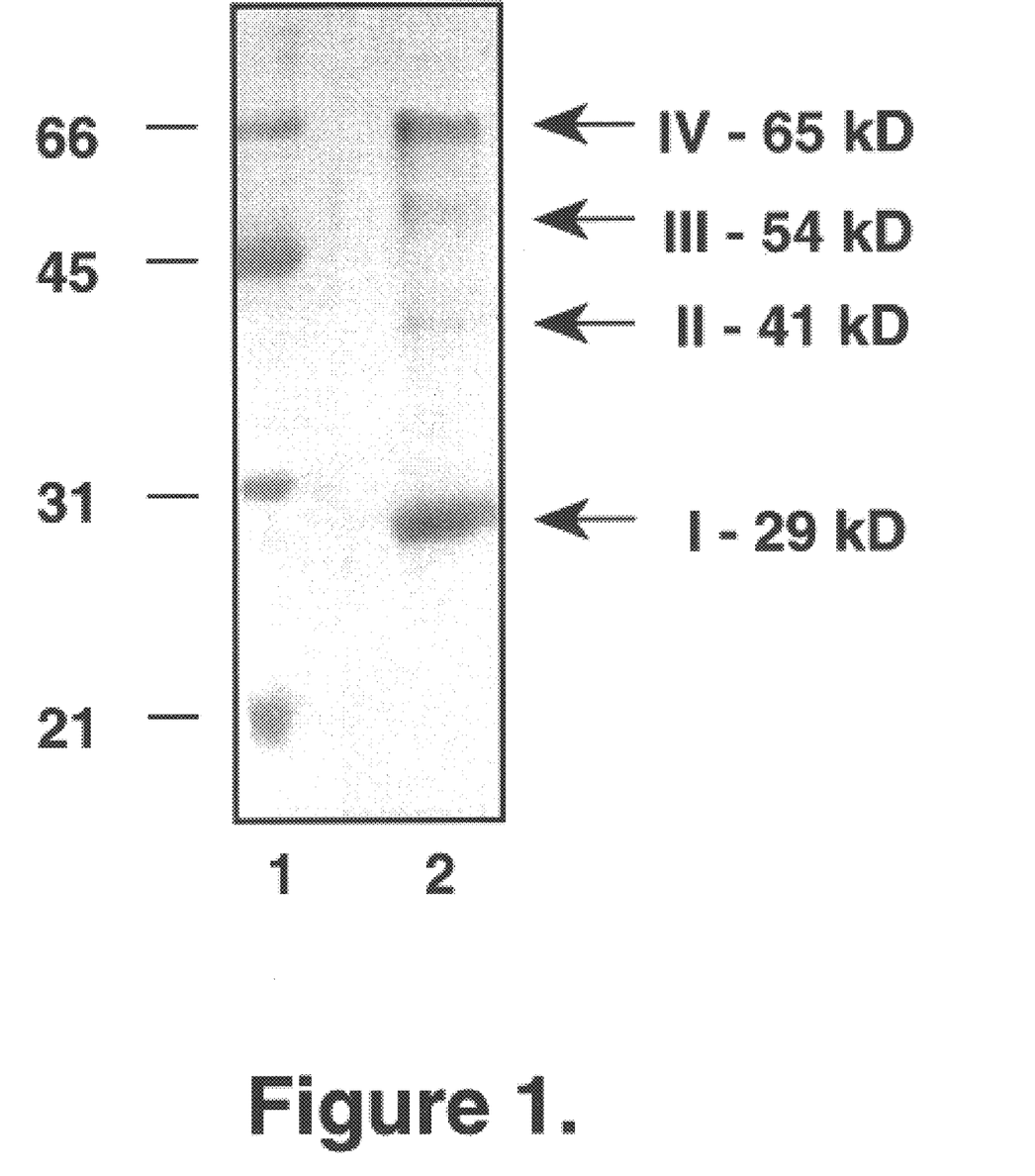
FIG. 1 shows the SDS PAGE gel analysis of the nectarins.

In accordance with the present invention, Nectarin I, II, III and/or IV, alone, or in any combination is used to treat diseases or conditions amenable to treatment by compounds having oxalate oxidase activity. Said conditions or diseases include, but are not limited to, kidney stones, primary oxaluria, and secondary oxaluria. SDS PAGE gel analysis of the nectarin proteins, as shown in FIG. 1, reveals the molecular weights of the nectarins. Lane 1 of FIG. 1 is the molecular weight marker of 14, 21, 31, 45, and 66 kDa. Lane 2 of FIG. 1 is the nectarins, which are identified by Roman numerals. Nectarin I has a molecular weight of about 29 kDa; Nectarin II about 41 kDa; Nectarin III about 54 kDa; and Nectarin IV about 65 kDa. Accordingly, the nectarins are also useful as molecular weight markers.

Nectarin may be administered orally, intravenously, intranasally, rectally, or by any means which delivers an effective amount to the organ, tissue or site to be treated. Suitable dosages are those which achieve the desired end point. It will be appreciated that different dosages may be required for treating different diseases or conditions related to abnormal deposition of oxalate. An effective amount of a nectarin is that amount which provides sufficient oxalate oxidase activity to cleave oxalate. Those having ordinary skill in the art will be able to ascertain the most effective dose and times for administering a nectarin, considering route of delivery, metabolism of nectarin, and other pharmacokinetic parameters such as volume of distribution, clearance, age of the subject, etc.

Nectarin may be administered along with a pharmaceutical carrier and/or diluent. Nectarin may be administered as the intact protein or as a fragment thereof, or as combinations of these. A fragment of nectarin useful in the present invention will be some portion of nectarin which possesses sufficient oxalate oxidase activity. As used herein, "nectarin" also includes derivatives of nectarin which contain one or more substitutions of amino acids in the primary amino acid sequence of the nectarin, but which still possess oxalate oxidase activity. Nectarin may also be administered in combination with other agents, for example, in association with other drugs or therapeutic agents useful in treating diseases or disorders associated with abnormal deposition of oxalate.

Nectarins may also be used to catalyze the cleavage of oxalate in specimens. Said specimens may include, but are not limited to, animal tissue, animal fluids, plant tissue, plant fluids and microbial cells or cell cultures. In some cases, it may be desirable to measure the amount of oxalate in a specimen. These cases include, but are not limited to, urolithiasis, primary oxaluria, secondary oxaluria, and ethylene glycol poisoning. The nectarins thus may be used to assess the amount of oxalate present in said specimens. Preferably, Nectarin I is used to measure the amount of oxalate in a specimen. In some cases, it may be desirable to conduct pre-analytical processing of the specimen. For example, tissue, urine or blood samples may require pre-analytical extraction using techniques known to those skilled in the art to prepare a specimen for oxalate determination. A sufficient amount of nectarin is incubated for a sufficient time with a specimen to catalyze the degradation of oxalate in the specimen. Those skilled in the art will be able to ascertain a sufficient amount of nectarin and time based on factors such as the amount of nectarin added to the specimen, the amount of specimen tested, and enzyme reaction kinetics. The oxalate degradation products of carbon dioxide and hydrogen peroxide are detected using standard clinical chemistry techniques such as, but not limited to, absorbance, coupled enzymatic reactions, and chromatography.

The following examples illustrate the teachings of the present invention and are not intended as limiting the scope of the invention.

EXAMPLES

Example 1
Determination of Nectarin I Amino Acid Sequence

This example describes the determination of the N-terminal amino acid sequence of secreted Nectarin I.

Interspecific crosses between *Nicotiana langsdorffii* and *Nicotiana sanderae* were prepared. Flowers were picked from these Nicotiana crosses and stored on ice. Nectar was collected by inserting a Pasteur pipet into the basal end of the inflorescence and applying suction. The typical yield of nectar from each inflorescence was about 25 microliters. Pooled nectar from multiple collections was concentrated by centrifugal ultrafiltration using a 30,000 dalton cutoff centrifuge filter (MSI; Westboro, Mass.). An equal volume of electrophoresis loading buffer (0.125 M Tris, pH 6.8, 4% SDS, 10% glycerol, 0.02% bromophenol blue, 4% β-mercaptoethanol) was added to the concentrated nectar. The nectar-buffer mixture was heated to 72° C. for 3 minutes and loaded onto a SDS-PAGE gel. The composition of the gel was as follows: stacking gel: 0.125 M Tris, pH 6.8, 0.2% SDS, 5% acrylamide:bisacrylamide (29:1); separating gel: 0.375 M Tris, pH 8.8, 0.4% SDS, 12% acrylamide:bisacrylamide (29:1). Electrophoresis was performed in a solution of 0.025 M Tris, pH 8.3, 0.2 M glycine, 1% SDS, A portion of the gel was stained with a solution of 0.2% coomassie blue, 10% acetic acid, 50% methanol, and 40% $H_2O$ to visualize the proteins and to determine the location of the nectarins. Using the stained portion of the gel as a guide, the Nectarin I band in the unstained portion of the gel was excised. The excision of a single species of protein was possible because of the limited number of proteins found in nectar. Nectarin I was transferred onto nylon membrane using an electroblot device (BioRad, Richmond, Calif.) in a solution of 0.012 M Tris, pH 8.3, 0.1 M glycine, 0.25% SDS. Half of the purified Nectarin I was used for the determination of the N-terminus sequence in a solid phase protein sequencer (Applied Biosystems, Foster City, Calif.). To determine internal sequence, the other half of the purified Nectarin I was cleaved with cyanogen bromide and the resultant fragments were individually purified by HPLC and sequenced.

The Nectarin I N-terminal amino acid sequence was found to be as follows:

SEQ. ID. No. 1: DEDMLQDVCVADLHSKVKVNGF-PCK

Figure 2:
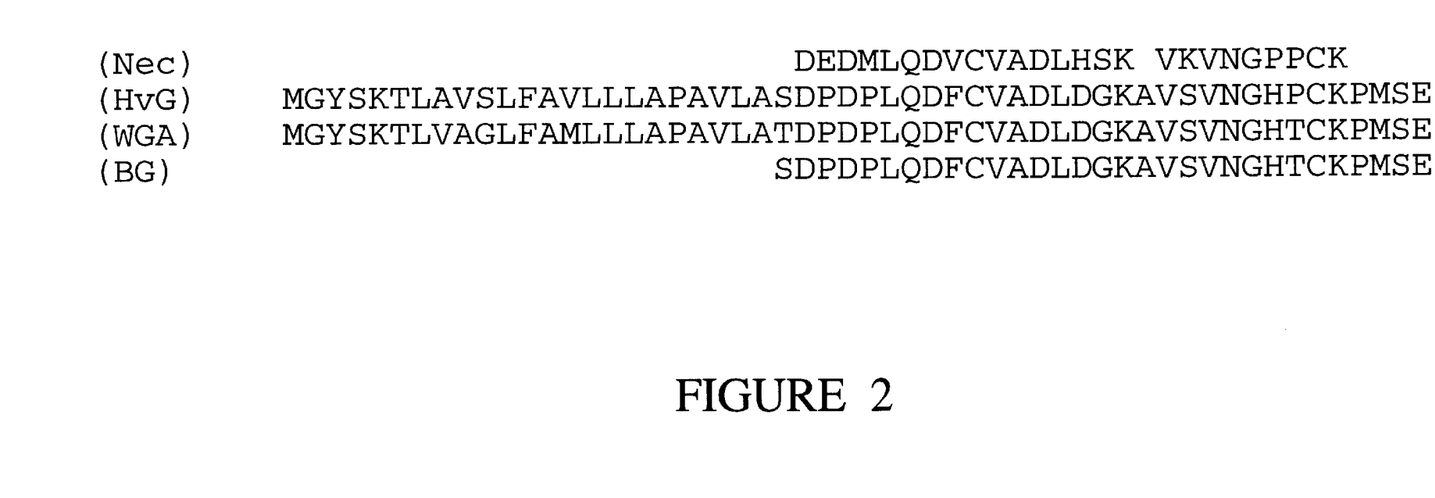
FIG. 2 shows the N-terminal amino acid sequence of Nectarin I (Nec) and the N-terminal amino acid sequence of Germin.

A BLAST search of Genbank showed identity between Nectarin I and the class of compounds called Germins (FIG. 2). In this figure, Nectarin I is identified as Nec. Germins are identified as BG (Barley Germin), WGA (Wheat Germin A), and HVG (Hordeum vulgare Germin CM 72).

Example 2

Isolation of Full-length Nectarin

This example describes the technique for isolating full-length nectarins. Antibodies to nectarins were first produced. In a prophetic example, the antibodies can be used to isolate full-length nectarins.

To produce polyclonal antibodies against nectarins from rabbits, 500 μg of nectarin in a volume of 100 μl was mixed vigorously with 100 μl of complete Freund's adjuvant. The resultant water and oil emulsion was injected subcutaneously into 8 week old New Zealand rabbits. The rabbits were boosted monthly with an oil and water emulsion of 200 μg of Nectarins in a volume of 100 μl and 100 μl of incomplete Freund's adjuvant. Antibodies were collected by removing 10 mls of blood 10 days after each boost. Blood was allowed to clot for 60 minutes at 37° C. and 16 hours at 4° C. after collection. Serum was separated from the clot by centrifugation for one hour at 10,000×g.

The remainder of this example is prophetic.

A nectarin affinity column is prepared for the purification of the polyclonal antibodies. To crosslink antigen to agarose, 5 mls of cyanogen bromide activated agarose (Pharmacia, Piscataway, N.J.) is added to 2 mg of nectarins in a 10 ml solution of 0.5 M sodium phosphate pH 7.5. Crosslinking proceeds for 8 hours in a shaker at room temperature. Uncrosslinked proteins are removed by washing the agarose with 0.5 M sodium phosphate pH 7.5. The remaining active sites are blocked by incubating the agarose in 100 mls of 100 mM ethanolamine pH 7.5. The agarose is ready for use after removal of ethanolamine by washes of phosphate buffered saline (0.21 g $KH_2PO_4$, 9 g NaCl, 0.726 g $Na_2HPO_4$, 1L $H_2O$).

An equal volume of serum is applied to the nectarin crosslinked column. Proteins and non-specific antibodies are removed by washing with 20 column volumes of phosphate buffered saline. Specific antibodies are eluted with 100 mM glycine buffer pH 2.5. The eluted antibodies are immediately neutralized with Tris pH 8.0 until the pH of the solution is at 7.5. Antibodies to nectarins are thus obtained.

Expression cDNA libraries of tobacco are available commercially (Stratagene, La Jolla, Calif.). Two million plaques of a cDNA expression library is screened using anti-nectarin antibodies. Briefly, 2,000,000 plaques are plated on a lawn of *E. coli* and the infected bacteria are induced to express their inserts with IPTG. The expressed proteins are transferred to nitrocellulose and probed with anti-nectarin antibody. The positive plaques are purified by multiple rounds of screening. By coinfecting *E. coli* with the positive phages and with helper phage R408, the phage vectors are converted into plasmid expression vectors. These plasmids are transformed into *E. coli* and induced to express their inserts. Individual preparations of the expressed proteins are purified by affinity chromatography using a cyanogen activated agarose crosslinked to nectarin antibody. The purified expressed proteins are sequenced using a protein sequencer and the sequence of the full-length nectarin is thus obtained.

Example 3

Determination of the Nectarin Signal Sequence

This is a prophetic example showing how the amino acid sequence of a signal peptide may be obtained.

A comparison of the amino acid sequence derived from the expressed nectarin with the amino acid sequence from secreted nectarin (as shown in Example 1) will reveal the signal peptide amino acid sequence. To further confirm that the nectarin signal peptide is properly identified, the plasmid expressing nectarin cDNA is sequenced using the dideoxy chain termination method. The signal peptide, being an amino terminal sequence, should begin with a methionine residue. The remainder of the peptide sequence should concur with the amino terminal sequence derived from protein sequencing.

Example 4

The Expression of Human Interferon in Nectar

This is a prophetic example demonstrating the expression of a protein non-native to a plant using the signal peptide of the present invention.

A double stranded sequence encoding the nectarin signal peptide followed by six histidines is synthesized using an oligonucleotide synthesizer (Applied Biosystems, Foster City, Calif.). The human alpha interferon gene is ligated 3' of a sequence encoding the nectarin signal peptide. This coding DNA is ligated between the strong constitutive Cauliflower Mosaic Virus 35S promoter and the efficient potato proteinase inhibitor II terminator. The sequence is arranged such that a transcript beginning at the Cauliflower Mosaic Virus promoter will transcribe through the signal peptide, the human interferon gene and terminate at the potato proteinase inhibitor II terminator.

Because the 200 kb Ti plasmid is too large for direct cloning methods, an integrative intermediate vector such as pMON200-HuINT may have to be used. The nectarin/interferon fusion gene is excised with EcoRI and transferred to the EcoRI site of pMON200 to create pMON200-HuINT. Proper insertion and transformation of pMON200-HuINT is further verified by transformation of bacteria strain LE392, by spectinomycin (50 μg/ml) selection, and by DNA sequencing.

The three bacteria involved in triparental conjugation are *E. coli* LE392 containing pMON200-HuINT, *E. coli* MM294 containing the mobilization plasmid, pRK2013, and *A. tumefaciens* strain GV3111SE containing the disarmed octopine type plasmid pTiB6S3SE. In triparental mating, the pRK2013 plasmid mobilizes into the *E. coli* containing pMON200-HuINT. Once within the *E. coli*/pMON200-HuINT cell, pRK2013 provides RK2 transfer proteins and the ColE1 mob protein, which acts on the bom site of pMON200-HuINT plasmid and thereby mobilizes the plasmid into *A. tumefaciens*. With pMON200-HuINT in *A. tumefaciens*, a few of the plasmids integrate into the resident disarmed pTiB6S3SE plasmid through homologous recombination with the LIH segment of the Ti plasmid and the LIH T-DNA segment in pMON200. Since the pMON200-HuINT cannot replicate in *A. tumefaciens*, by selection with chloramphenicol, kanamycin, streptomycin, and spectinomycin, one is selecting only those *A. tumefaciens* in which pMON200-HuINT has cointegrated into the Ti plasmid.

The three bacteria involved in triparental conjugation and their culture conditions are listed below:

| Bacteria Strain and Plasmid | Culture Conditions |
|---|---|
| Strain 1 | LB broth |
| E. coli strain LE392 containing the Nectarin-human interferon fusion gene pMON200-HuINT. | 50 μg/ml spectinomycin 37° C. |
| Strain 2 | LB broth |
| E. coli strain MM294 containing the mobilization plasmid pRK2013 | 50 μg/ml kanamycin 37° C. |
| Strain 3 | LB broth |
| A. tumefaciens strain GV3111SE (C58C1, chloramphenicol resistant, $C_m^R$) carrying the disarmed octopine type plasmid, pTiB6S3SE tra. | 25 μg/ml chloramphenicol 50 μg/ml kanamycin 28° C. |

To facilitate recombination of plasmids in all three bacteria, combine 1 ml of each bacteria culture in a sterile tube. Transfer the bacteria to a magnesium solution by centrifuging the tube at 5000×g and resuspend the bacteria in 2 ml of 10 mM $MgSO_4$. Concentrate the bacteria onto one filter by filtering the bacteria solution in a Swinney filter apparatus (Millipore, Bedford, Mass.). The filter disk containing all the bacteria is removed and transferred sterilely onto a fresh LB agar plate with the bacteria side on top. The bacteria are allowed to recover from transformation by 16 hours growth on non-selective LB plates. Collect bacteria for selection by vortexing the filter disk in 2 ml of 10 mM $MgSO_4$. Select for transformed A. tumefaciens and kill the E. coli by plating 20 aliquots of the 2 ml solution onto 20 LB plates containing chloramphenicol 25 μg/ml, kanamycin 50 μg/ml, streptomycin 100 μg/ml, and spectinomycin 100 μg/ml. To ensure the complete removal of untransformed A. tumefaciens, the positive colonies are picked and grown at 28° C. liquid culture with chloramphenicol 25 μg/ml, kanamycin 50 μg/ml, streptomycin 100 μg/ml, and spectinomycin 100 μg/ml for 24 hours.

For the transformation of plant cells, collect healthy, unblemished leaves from young tobacco plants and immersed in 4 liters of 10% solution of commercial bleach (Clorox) with 10 drops of Tween 20 added. Agitate the solution gently for 20 minutes and wash the leaves three times with sterile distilled $H_2O$. Visually examine the leaves and discard any which show damage from the bleach. Form explants by cutting disks of about 6 mm in size from the leaves with a sterile paper punch. To transform the plant tissue, place one explant and 1 ml of the bacteria culture in a tube and shake gently for 10 seconds. Remove the explant and blot it dry with sterile paper. The resultant explants are used to regenerate transformed plants.

Allow the transformed cells to establish sizable colonies by culturing the explants upside down on culture plates containing 0.8% agar; 1×MS salts (Gibco); 1×B5 vitamins; 30 g/L sucrose; 1 μg/ml benzyladenine and 0.1 μg/ml naphthaleneacetic acid with a pH of 5.7 for five days. To regenerate plants, transfer the explants to culture plates containing 0.8% agar; 1×B5 vitamins; 30 g/L sucrose; 1 μg/ml benzyladenine and 0.1 μg/ml naphthaleneacetic acid; 500 μg/ml carbenicillin; 300 μg/ml kanamycin sulfate; and 500 μg/ml Cefotaxime (Calbiochem, La Jolla, Calif.) with a pH of 5.7. The explants are cultured and selected for 4 weeks to allow shoots to develop. Only the shoots which develop from this culture are cut and induced to grow roots by growth in rooting plates containing 0.8% agar; 1×B5 vitamins; 30 g/L sucrose; 500 μg/ml carbenicillin and 300 μg/ml kanamycin sulfate with a pH of 5.7. Those shoots that root in the rooting agar are transferred to soil.

The shoots with roots are collected when the roots are 3 mm in length. Individual shoots are transferred to sterile planting mix in 2.25 inch square pots that fit within GA7 containers (Magenta Corp., Chicago, Ill.). The plantlet is allowed to establish a root system by growing in the GA7 container with the lid tightly capped. To ensure survival, the shootlets should be adapted to grow at regular humidity level very slowly. Excess $H_2O$ within the container is allowed to evaporate by opening the lid until a crack of less than one mm appears. After two days of growth, the crack is enlarged to 2 mm and the plantlet is allowed to grow for two more days. To finish hardening the plant, slowly increase the size of the crack about 1 mm a day until the lid is completely open.

The resultant plants can now be transferred to soil and grown under conditions suitable for tobacco. Collect flowers from the resultant plants and remove the nectar by suction. Save the plants that show the highest level of foreign protein or recombinant protein expression in the nectar.

Example 5

Purification of Human Interferon from Nectar

This is a prophetic example showing the use of a nickel affinity column and tagged signal peptide to purify a non-native protein.

Phosphate buffers are used in nickel affinity column chromatography because they do not interfere with binding. The pH of phosphate buffers drift and should be prepared fresh each day. Prepare a solution of 20 mM Na-phosphate monobasic, 20% glycerol, 2 mM β-mercaptoethanol, 100 mM KCl and a solution of 20 mM Na-phosphate dibasic, 20% glycerol, 2 mM β-mercaptoethanol, 100 mM KCl. Mix the two solutions to adjust the pH to 7.9.

To remove low molecular weight contaminants and carbohydrates, dialyze nectar against phosphate buffer pH 7.6 three times for 4 hours each at 4° C. Apply the dialyzed nectar onto a 5 ml nickel column (Invitrogen, San Diego, Calif.). Remove unbound contaminants by washing the column with pH 7.9 phosphate buffer. Monitor the concentration of proteins removed by measuring optical density at 280 nm. This wash should require about 20 column volumes.

Remove weakly bound proteins by washing the nickel column with about 10 column of a pH 6.0 phosphate buffer. The affinity tagged interferon can be eluted with a phosphate buffer of pH 4.0. Elute the interferon slowly with 2 column volumes of phosphate pH 4.0 buffer. Collect 0.1 column volume fractions (0.5 ml) and assay the protein in each fraction by measurement of optical density at 280 nm. Pool the peak fractions containing purified human interferon and add Tris pH 8.0 to adjust the pH of the eluate to 7.5.

Example 6

Determination of Oxalate Oxidase Activity

Figure 3:
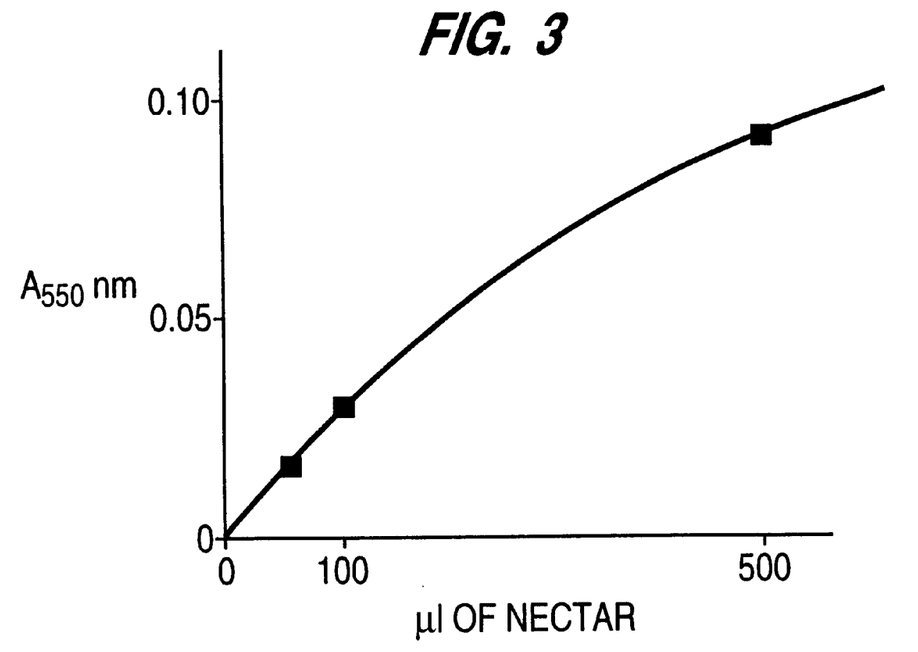
FIG. 3 shows the oxalate oxidase activity of nectar.

In this example, it is shown that nectar possesses oxalate oxidase activity. As shown in Example 1, the N-terminal sequence of Nectarin I has some similarity to Germins. The function of Germin has been identified at oxalate oxidase. Lane, B. et al., J. Biol. Chem. 268: 12,239–12,242 (1993). Various amounts of nectar from fresh Nicotiana sp., were tested for oxalate oxidase activity using the method of Sugiura, et al. Chem. Pharm. Bull. 22: 2003 (1979). Oxalate oxidase activity was monitored by absorbance at 550 nm in a spectrophotometer. Results, shown in FIG. 3, reveal that nectar possesses oxalate oxidase activity.

Example 7

Identification of Oxalate Oxidase Activity

This is a prophetic example. To show that nectarin has oxalate oxidase activity, collect nectar and subject it to SDS-PAGE analysis and transferred to nitrocellulose filter paper using procedures described in Example 1. Oxalate oxidase activity is detected by immersing the filter paper in a solution made by combining 5 ml of substrate solution (2 mM oxalate, 100 mM succinate pH 3.5) with 3 mls of developing solution (0.25 mg of 4-aminoantipyrine, 40 units of horseradish peroxidase) and with 0.6 µl of N,N-dimethylaniline in 100 mM sodium phosphate pH 5.5. After 20 minutes at room temperature, the filter is rinsed with $H_2O$ and areas of oxalate oxidase activity will cause oxalate dependent release of $H_2O_2$, which is manifested as a blue band on the blot.

Many other variations and modifications may be made in the techniques herein before described, by those having skill in this technology, without departing from the concept of the present invention. Accordingly, it should be clearly understood that the foregoing description is illustrative only, and not intended as a limitation on the scope of the invention.

---

What is claimed is:

1. A method for expressing at least one protein into nectar comprising introducing into a plant cell a nucleic acid construct comprising DNA that encodes a Nicotiana nectarin signal peptide and at least one protein, wherein said signal peptide facilitates secretion of said at least one protein from said plant cell into said nectar.

2. The method according to claim 1 wherein said nucleic acid construct comprises DNA that encodes at least one protein non-native to said plant or at least one protein native to said plant, or combinations thereof.

3. The method according to claim 2 wherein said at least one protein non-native to said plant is selected from the group consisting of lipase, pigments, hormones, growth factors, interleukins, EPO, G-CSF, GM-CSF, hPG-CSF, M-CSF, Factor VIII, Factor IX, tPA, hGH, receptors, insulin, interferon, antithrombin III, glucagon, vaccines, affinity tags, antibiotics, and combinations thereof.

4. The method according to claim 2 wherein said DNA encodes at least one affinity tag and at least one protein native or at least one protein non-native to said plant, wherein said at least one protein native or at least one protein non-native to said plant is covalently attached to said at least one affinity tag.

5. The method according to claim 4 wherein said affinity tag is selected from the group consisting of polyhistidine, FLAG antigen, antigens, antibodies, antibody fragments, receptors, maltose binding protein, biotin, and combinations thereof.

6. The method according to claim 2 wherein said at least one protein native to said plant is selected from the group consisting of proteinase inhibitor, chitinase, cutinase, cholesterol hydroxylase, SAM-protocatechuate methyl transferase, vanillic acid dehydrogenase, oxalate oxidase, peroxidase, papain, ribonuclease and protease.

7. A The method according to claim 1 wherein said plant cell is a species selected from a genus of the group consisting of Agave, Albizzia, Allium, Aloe, Ammi, Amoracia, Anagallis, Ananas, Andropogon, Anethum, Anthurium, Antirrhinum, Apium, Arabidopsis, Arachis, Asparagus, Atropa, Avena, Averrhoa, Begonia, Beta, Betula, Biota, Brachycome, Brassica, Bromus, Broussonetia, Browallia, Cajanus, Capsicum, Carica, Carum, Caucus, Centaurea, Ceratonia, Cheiranthus, Chrysanthemum, Cichorium, Citrus, Crotalaria, Coffea, Consolida, Convolvulus, Coptis, Conium, Cordyline, Coriandrum, Corylus, Crambe, Crassula, Crepis, Cupressus, Cucurbita, Cynara, Cyclamen, Dactylis, Datura, Daucus, Digitalis, Dioscorea, Diospyros, Dracaena, Drimys, Elaeis, Eleusine, Eschscholzia, Euphorbia, Fagopyrum, Festuca, Foeniculum, Gazania, Glycine, Gossypium, Haworthia, Hedera, Heloniopsis, Hemerocallis, Hordeum, Hyacinthus, Hyoscyamus, Iberis, Ilex, Indigofera, Ipomea, Iris, Lactuca, Lathyrus, Lilium, Limnophyla, Linum, Liquidambar, Lobularia, Lolium, Lotus, Lycopersicon, Macleaya, Malus, Mammillaria, Manihot, Mazus, Medicago, Mesembryanthemum, Muscari, Narcissus, Nemesia, Nicotiana, Nigella, Ornithogalum, Oryza, Panicum, Panox, Papaver, Parthenium, Parthenocissus, Paspalum, Passiflora, Paulownia, Pelargonium, Pennisetum, Peperomia, Pergularia, Perilla, Petraniva, Petroselium, Petunia, Phaseolus, Phoenix, Phlox, Phragmites, Physalis, Picea, Pimpinella, Pinus, Pisium, Populus, Prunus, Pseudotsuga, Psophocarpus, Pterotheca, Ranunculus, Rosa, Rubus, Saccharum, Salpiglossis, Santalum, Scopalia, Scilla, Sedum, Senecio, Sinapis, Sisymbrium, Sium, Solanum, Sorghastrum, Sorghum, Stevia, Stylosanthes, Taraxacum, Thalictrum, Theobroma, Tylophora, Thuja, Torenia, Trifolium, Trigonella, Triticale, Triticum, Ulmus, Verbascum, Vicia, Vigna, Vitis, Zea, and Zingiber.

8. The method according to claim 1 wherein said plant cell is selected from the group consisting of N. alata, N. tabacum, N. plumbaginifolia, N. langsdorffii, N. sanderae, and hybrids thereof.

9. The method according to claim 1 wherein said signal peptide is Nectarin I.

10. A purified nucleic acid construct comprising DNA that encodes a Nicotiana nectarin signal peptide and at least one protein, wherein said signal peptide facilitates secretion of said at least one protein from said plant into nectar.

11. The purified nucleic acid construct of claim 10 wherein said nucleic acid construct comprises DNA encoding at least one protein non-native to said plant or at least one protein native to said plant, or combinations thereof.

12. The purified nucleic acid construct of claim 11 wherein said protein non-native to said plant is selected from the group consisting of lipase, pigments, hormones, growth factors, interleukins, EPO, G-CSF, GM-CSF, hPG-CSF, M-CSF, Factor VIII, Factor IX, tPA, hGH, receptors, insulin, interferon, antithrombin III, glucagon, vaccines, affinity tags, antibiotics, and combinations thereof.

13. The purified nucleic acid construct of claim 11 wherein said DNA encodes at least one affinity tag and at least one protein native or at least one protein non-native to said plant, wherein said at least one protein native or at least one protein non-native to said plant is covalently attached to said at least one affinity tag.

14. The purified nucleic acid construct of claim 13 wherein said affinity tag is selected from the group consisting of polyhistidine, FLAG antigen, antigens, antibodies, antibody fragments, receptors, maltose binding protein, biotin and combinations thereof.

15. The purified nucleic acid construct of claim 11 wherein said protein native to said plant is selected from the group consisting of proteinase inhibitor, chitinase, cutinase, cholesterol hydroxylase, SAM-protocatechuate methyl transferase, vanillic acid dehydrogenase, oxalate oxidase, peroxidase, papain, ribonuclease and protease.

16. The purified nucleic acid construct of claim 10 wherein said plant is a species selected from a genus of the group consisting of Agave, Albizzia, Allium, Aloe, Ammi, Amoracia, Anagallis, Ananas, Andropogon, Anethum, Anthurium, Antirrhinum, Apium, Arabidopsis, Arachis, Asparagus, Atropa, Avena, Averrhoa, Begonia, Beta, Betula, Biota, Brachycome, Brassica, Bromus, Broussonetia, Browallia, Cajanus, Capsicum, Carica, Carum, Caucus, Centaurea, Ceratonia, Cheiranthus, Chrysanthemum, Cichorium, Citrus, Crotalaria, Coffea, Consolida, Convolvulus, Coptis, Conium, Cordyline, Coriandrum, Corylus, Crambe, Crassula, Crepis, Cupressus, Cucurbita, Cynara, Cyclamen, Dactylis, Datura, Daucus, Digitalis, Dioscorea, Diospyros, Dracaena, Drimys, Elaeis, Eleusine, Eschscholzia, Euphorbia, Fagopyrum, Festuca, Foeniculum, Gazania, Glycine, Gossypium, Haworthia, Hedera, Heloniopsis, Hemerocallis, Hordeum, Hyacinthus, Hyosqyamus, Iberis, Ilex, Indigofera, Ipomea, Iris, Lactuca, Lathyrus, Lilium, Limnophyla, Linum, Liquidambar, Lobularia, Lolium, Lotus, Lycopersicon, Macleaya, Malus, Mammillaria, Manihot, Mazus, Medicago, Mesembryanthemum, Muscari, Narcissus, Nemesia, Nicotiana, Nigella, Ornithogalum, Oryza, Panicum, Panox, Papaver, Parthenium, Parthenocissus, Paspalum, Passiflora, Paulownia, Pelargonium, Pennisetum, Peperomia, Pergularia, Perilla, Petraniva, Petroselium, Petunia, Phaseolus, Phoenix, Phlox, Phragmites, Physalis, Picea, Pimpinella, Pinus, Pisium, Populus, Prunus, Pseudotsuga, Psophocarpus, Pterotheca, Ranunculus, Rosa, Rubus, Saccharum, Salpiglossis, Santalum, Scopalia, Scilla, Sedum, Senecio, Sinapis, Sisymbrium, Sium, Solanum, Sorghastrum, Sorghum, Stevia, Stylosanthes, Taraxacum, Thalictrum, Theobronma, Tylophora, Thuja, Torenia, Trifolium, Trigonella, Triticale, Triticum, Ulmus, Verbascum, Vicia, Vigna, Vitis, Zea, and Zingiber.

17. The purified nucleic acid construct of claim 10 wherein said plant is selected from the group consisting of N. alata, N. tabacum, N. plumbaginifolia, N. langsdorffii, N. sanderae, and hybrids thereof.

18. The purified nucleic acid construct of claim 10 wherein said signal peptide is Nectarin I.

19. The purified nucleic acid construct of claim 10 further comprising at least one element selected from the group consisting of transcription promoters, enhancers, initiation sites, RNA splicing sites, endonuclease cleavage sites, termination sites, polyadenylation sites, selectable markers, screenable markers, and combinations thereof.

20. The purified nucleic acid construct of claim 19 wherein said promoter is selected from the group consisting of cauliflower mosaic virus promoters, potato proteinase inhibitor promoters, and combinations thereof.

21. The purified nucleic acid construct of claim 20 wherein said promoter is inducible.

22. The purified nucleic acid construct of claim 21 wherein said inducible promoter is selected from the group consisting of thermal inducible promoters, metal inducible promoters, wound inducible promoters, hormone inducible promoters, photosensitive inducible promoters, gas inducible promoters, pathogen inducible promoters, stress inducible promoters, and combinations thereof.

23. The purified nucleic acid construct of claim 19 wherein said selectable marker is selected from the group consisting of thymidine kinase, dihydrofolate reductase, animoglycoside phosphotransferase, hygromycin B phosphotransferase, xanthine-guanine phosphoribosyl transverse, CAD protein, adenosine deaminase, neomycin phosphototransferase, chloramphenicol acetyl transferse, asparagine synthetase, herbicide resistance genes, metallothionine, cytosine deaminase, and combinations thereof.

24. A recombinant vector comprising DNA that encodes a Nicotiana nectarin signal peptide and at least one protein, wherein said signal peptide facilitates secretion of said at least one protein from a plant into nectar.

25. The recombinant vector of claim 24 wherein said vector comprises DNA that encodes a protein non-native to said plant or a protein native to said plant, or combinations thereof.

26. The recombinant vector of claim 25 wherein said protein non-native to said plant is selected from the group consisting of lipase, pigments, hormones, growth factors, interleukins, EPO, G-CSF, GM-CSF, hPG-CSF, M-CSF, Factor VIII, Factor IX, tPA, hGH, receptors, insulin, interferon, antithrombin III, glucagon, vaccines, affinity tags, antibiotics, and combinations thereof.

27. The recombinant vector of claim 25 wherein said DNA encodes at least one affinity tag and at least one protein native or at least one protein non-native to said plant, wherein said at least one protein native or at least one protein non-native to said plant is covalently attached to said at least one affinity tag.

28. A The recombinant vector of claim 27 wherein said affinity tag is selected from the group consisting of polyhistidine, FLAG antigen, antigens, antibodies, antibody fragments, receptors, maltose binding protein, and combinations thereof.

29. The recombinant vector of claim 25 wherein said protein native to said plant is selected from the group consisting of proteinase inhibitor, chitinase, cutinase, cholesterol hydroxylase, SAM-protocatechuate methyl transferase, vanillic acid dehydrogenase, oxalate oxidase, peroxidase, papain, ribonuclease and protease.

30. The recombinant vector of claim 24 wherein said plant is a species selected from a genus of the group consisting of Agave, Albizzia, Allium, Aloe, Ammi, Amoracia, Anagallis, Ananas, Andropogon, Anethum, Anthurium, Antirrhinum, Apium, Arabidopsis, Arachis, Asparagus, Atropa, Avena, Averrhoa, Begonia, Beta, Betula, Biota, Brachycome, Brassica, Bromus, Broussonetia, Browallia, Cajanus, Capsicum, Carica, Carum, Caucus, Centaurea, Ceratonia, Cheiranthus, Chrysanthemum, Cichorium, Citrus, Crotalaria, Coffea, Consolida, Convolvulus, Coptis, Conium, Cordyline, Coriandrum, Corylus, Crambe, Crassula, Crepis, Cupressus, Cucurbita, Cynara, Cyclamen, Dactylis, Datura, Daucus, Digitalis, Dioscorea, Diospyros, Dracaena, Drimys, Elaeis, Eleusine, Eschscholzia, Euphorbia, Fagopyrum, Festuca, Foeniculum, Gazania, Glycine, Gossypium, Haworthia, Hedera, Heloniopsis, Hemerocallis, Hordeum, Hyacinthus, Hyoscyamus, Iberis, Ilex, Indigofera, Ipomea, Iris, Lactuca, Lathyrus, Lilium, Limnophyla, Linum, Liquidambar, Lobularia, Lolium, Lotus, Lycopersicon, Macleaya, Malus, Mammillaria, Manihot, Mazus, Medicago, Mesembryanthemum, Muscari, Narcissus, Nemesia, Nicotiana, Nigella, Ornithogalum, Oryza, Panicum, Panox, Papaver, Parthenium, Parthenocissus, Paspalum, Passiflora, Paulownia, Pelargonium, Pennisetum, Peperomia, Pergularia, Perilla, Petraniva, Petroselium, Petunia, Phaseolus, Phoenix, Phlox, Phragmites, Physalis, Picea, Pimpinella, Pinus, Pisium, Populus, Prunus, Pseudotsuga, Psophocarpus, Pterotheca, Ranunculus, Rosa, Rubus, Saccharum, Salpiglossis, Santalum, Scopalia, Scilla, Sedum, Senecio, Sinapis, Sisymbrium, Sium, Solanum, Sorghastrum, Sorghum, Stevia, Stylosanthes, Taraxacum, Thalictrum, Theobroma, Tylophora, Thuja, Torenia, Trifolium, Trigonella, Triticale, Triticum, Ulmus, Verbascum, Vicia, Vigna, Vitis, Zea, and Zingiber.

31. The recombinant vector of claim 24 wherein said plant is selected from the group consisting of *N. alata, N. tabacum, N. plumbaginifolia, N. langsdorffi, N. sanderae*, and hybrids thereof.

32. The recombinant vector of claim 24 wherein said signal peptide is Nectarin I.

33. The vector of claim 24 which is selected from the group consisting of plasmids, cosmids, phages, viral vectors, artificial chromosomes and combinations thereof.

34. The recombinant vector of claim 33 wherein said plasmid is derived from *Agrobacterium tumefaciens* or *A. rhizogenes*.

35. A recombinant plant cell comprising a nucleic acid construct comprising DNA that encodes a Nicotiana nectarin signal sequence and at least one protein, wherein said signal sequence facilitates extracellular secretion into nectar of said at least one protein from a plant cell.

36. The recombinant plant cell of claim 35 wherein said nucleic acid construct comprises DNA that encodes at least one protein non-native to said plant or at least one protein native to said plant, or combinations thereof.

37. The recombinant plant cell of claim 36 wherein said protein non-native to said plant is selected from the group consisting of lipase, pigments, hormones, growth factors, interleukins, EPO, G-CSF, GM-CSF, hPG-CSF, M-CSF, Factor VIII, Factor IX, tPA, hGH, receptors, insulin, interferon, antithrombin III, glucagon, vaccines, asparagine synthase, herbicide resistance genes, metallothionine, cytesine deaminase, antibiotics, and combinations thereof.

38. The recombinant plant cell of claim 36 wherein said protein native to said plant is selected from the group consisting of proteinase inhibitor, chitinase, cutinase, cholesterol hydroxylase, SAM-protocatechuate methyl transferase, vanillic acid dehydrogenase, oxalate oxidase, peroxidase, papain, ribonuclease and protease.

39. The recombinant plant cell of claim 36 wherein said plant cell is a species selected from a genus of the group consisting of Agave, Albizzia, Allium, Aloe, Ammi, Amoracia, Anagallis, Ananas, Andropogon, Anethum, Anthurium, Antirrhinum, Apium, Arabidopsis, Arachis, Asparagus, Atropa, Avena, Averrhoa, Begonia, Beta, Betula, Biota, Brachycome, Brassica, Bromus, Broussonetia, Browallia, Cajanus, Capsicum, Carica, Carum, Caucus, Centaurea, Ceratonia, Cheiranthus, Chrysanthemum, Cichorium, Citrus, Crotalaria, Coffea, Consolida, Convolvulus, Coptis, Conium, Cordyline, Coriandrum, Corylus, Crambe, Crassula, Crepis, Cupressus, Cucurbita, Cynara, Cyclamen, Dactylis, Datura, Daucus, Digitalis, Dioscorea, Diospyros, Dracaena, Drimys, Elaeis, Eleusine, Eschscholzia, Euphorbia, Fagopyrum, Festuca, Foeniculum, Gazania, Glycine, Gossypium, Haworthia, Hedera, Heloniopsis, Hemerocallis, Hordeum, Hyacinthus, Hyoscyamus, Iberis, Ilex, Indigofera, Ipomea, Iris, Lactuca, Lathyrus, Lilium, Limnophyla, Linum, Liquidambar, Lobularia, Lolium, Lotus, Lycopersicon, Macleaya, Malus, Mammillaria, Manihot, Mazus, Medicago, Mesembryanthemum, Muscari, Narcissus, Nemesia, Nicotiana, Nigella, Ornithogalum, Oryza, Panicum, Panox, Papaver, Parthenium, Parthenocissus, Paspalum, Passiflora, Paulownia, Pelargonium, Pennisetum, Peperomia, Pergularia, Perilla, Petraniva, Petroselium, Petunia, Phaseolus, Phoenix, Phlox, Phragmites, Physalis, Picea, Pimpinella, Pinus, Pisium, Populus, Prunus, Pseudotsuga, Psophocarpus, Pterotheca, Ranunculus, Rosa, Rubus, Saccharum, Salpiglossis, Santalum, Scopalia, Scilla, Sedum, Senecio, Sinapis, Sisymbrium, Sium, Solanum, Sorghastrum, Sorghum, Stevia, Stylosanthes, Taraxacum, Thalictrum, Theobroma, Tylophora, Thuja, Torenia, Trifolium, Trigonella, Triticale, Triticum, Ulmus, Verbascum, Vicia, Vigna, Vitis, Zea, and Zingiber.

40. The recombinant plant cell of claim 36 wherein said plant cell is selected from the group consisting of *N. alata, N. tabacum, N. plumbaginifolia, N. langsdorffii, N. sanderae*, and hybrids thereof.

41. The recombinant plant cell of claim 36 wherein said signal sequence is Nectarin I.

42. A recombinant plant comprising a nucleic acid construct comprising DNA that encodes a Nicotiana nectarin signal sequence and at least one protein wherein said signal sequence facilitates extracellular secretion into nectar of said at least one protein from a plant.

43. The recombinant plant of claim 42 wherein said protein is non-native to said plant or native to said plant, or combinations thereof.

44. The recombinant plant of claim 43 wherein said protein non-native to said plant is selected from the group consisting of lipase, pigments, hormones, growth factors, interleukins, EPO, G-CSF, GM-CSF, hPG-CSF, M-CSF, Factor VIII, Factor IX, tPA, hGH, receptors, insulin, interferon, antithrombin III, glucagon, vaccines, asparagine synthase, herbicide resistance genes, metallothionine, cytesine deaminase, antibiotics, and combinations thereof.

45. The recombinant plant of claim 43 wherein said protein native to said plant is selected from the group consisting of proteinase inhibitor, chitinase, cutinase, cholesterol hydroxylase, SAM-protocatechuate methyl transferase, vanillic acid dehydrogenase, oxalate oxidase, peroxidase, papain, ribonuclease and protease.

46. The recombinant plant of claim 43 wherein said plant is a species selected from a genus of the group consisting of Agave, Albizzia, Allium, Aloe, Ammi, Amoracia, Anagallis, Ananas, Andropogon, Anethum, Anthurium, Antirrhinum, Apium, Arabidopsis, Arachis, Asparagus, Atropa, Avena, Averrhoa, Begonia, Beta, Betula, Biota, Brachycome, Brassica, Bromus, Broussonetia, Browallia, Cajanus, Capsicum, Carica, Carum, Caucus, Centaurea, Ceratonia, Cheiranthus, Chrysanthemum, Cichorium, Citrus, Crotalaria, Coffea, Consolida, Convolvulus, Coptis, Conium, Cordyline, Coriandrum, Corylus, Crambe, Crassula, Crepis, Cupressus, Cucurbita, Cynara, Cyclamen, Dactylis, Datura, Daucus, Digitalis, Dioscorea, Diospyros, Dracaena, Drimys, Elaeis, Eleusine, Eschscholzia, Euphorbia, Fagopyrum, Festuca, Foeniculum, Gazania, Glycine, Gossypium, Haworthia, Hedera, Heloniopsis, Hemerocallis, Hordeum, Hyacinthus, Hyosqyamus, Iberis, Ilex, Indigofera, Ipomea, Iris, Lactuca, Lathyrus, Lilium, Limnophyla, Linum, Liquidambar, Lobularia, Lolium, Lotus, Lycopersicon, Macleaya, Malus, Mammillaria, Manihot, Mazus, Medicago, Mesembryanthemum, Muscari, Narcissus, Nemesia, Nicotiana, Nigella, Ornithogalum, Oryza, Panicum, Panox, Papaver, Parthenium, Parthenocissus, Paspalum, Passiflora, Paulownia, Pelargonium, Pennisetum, Peperomia, Pergularia, Perilla, Petraniva, Petroselium, Petunia, Phaseolus, Phoenix, Phlox, Phragmites, Physalis, Picea, Pimpinella, Pinus, Pisium, Populus, Prunus, Pseudotsuga, Psophocarpus, Pterotheca, Ranunculus, Rosa, Rubus, Saccharum, Salpiglossis, Santalum, Scopalia, Scilla, Sedum, Senecio, Sinapis, Sisymbrium, Sium, Solanum, Sorghastrum, Sorghum, Stevia, Stylosanthes, Taraxacum, Thalictrum, Theobroma, Tylophora, Thuja, Torenia, Trifolium, Trigonella, Triticale, Triticum, Ulmus, Verbascum, Vicia, Vigna, Vitis, Zea, and Zingiber.

47. The recombinant plant of claim 43 wherein said plant is selected from the group consisting of *N. alata, N. tabacum, N. plumbaginifolia, N. langsdorffii, N. sanderae*, and hybrids thereof.

48. The recombinant plant of claim 43 wherein said signal sequence is Nectarin I.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 25 amino acids
      (B) TYPE: amino acid
      (C) STRANDEDNESS: single
      (D) TOPOLOGY: linear    (ii) MOLECULE TYPE: peptide    (iii) HYPOTHETICAL: NO    (iv) ANTI-SENSE: NO    (v) FRAGMENT TYPE: N-terminal    (vi) ORIGINAL SOURCE:
      (A) ORGANISM: Nectarin 1

(xi) SEQUENCE DESCRIPTION: SEQ ID NO:1:

```
Asp Glu Asp Met Leu Gln Asp Val Cys Val Ala Asp Leu His Ser Lys
 1               5                  10                  15

Val Lys Val Asn Gly Phe Pro Cys Lys
                20                  25
```

(2) INFORMATION FOR SEQ ID NO:2:

(i) SEQUENCE CHARACTERISTICS:
      (A) LENGTH: 54 amino acids
      (B) TYPE: amino acid
      (C) STRANDEDNESS: single
      (D) TOPOLOGY: linear    (ii) MOLECULE TYPE: peptide    (iii) HYPOTHETICAL: NO    (iv) ANTI-SENSE: NO    (v) FRAGMENT TYPE: N-terminal    (vi) ORIGINAL SOURCE:
      (A) ORGANISM: Hordium vulgrae Germin CM72

(xi) SEQUENCE DESCRIPTION: SEQ ID NO:2:

```
Met Gly Tyr Ser Lys Thr Leu Ala Val Ser Leu Phe Ala Val Leu Leu
 1               5                  10                  15

Leu Ala Pro Ala Val Leu Ala Ser Asp Pro Asp Pro Leu Gln Asp Phe
                20                  25                  30

Cys Val Ala Asp Leu Asp Gly Lys Ala Val Ser Val Asn Gly His Pro
                35                  40                  45

Cys Lys Pro Met Ser Glu
                50
```

(2) INFORMATION FOR SEQ ID NO:3:

(i) SEQUENCE CHARACTERISTICS:
        (A) LENGTH: 54 amino acids
        (B) TYPE: amino acid
        (C) STRANDEDNESS: single
        (D) TOPOLOGY: linear    (ii) MOLECULE TYPE: peptide   (iii) HYPOTHETICAL: NO    (iv) ANTI-SENSE: NO     (v) FRAGMENT TYPE: N-terminal    (vi) ORIGINAL SOURCE:
       (A) ORGANISM: Wheat Germin A    (xi) SEQUENCE DESCRIPTION: SEQ ID NO:3:

```
Met Gly Tyr Ser Lys Thr Leu Val Ala Gly Leu Phe Ala Met Leu Leu
 1               5                  10                  15

Leu Ala Pro Ala Val Leu Ala Thr Asp Pro Asp Pro Leu Gln Asp Phe
            20                  25                  30

Cys Val Ala Asp Leu Asp Gly Lys Ala Val Ser Val Asn Gly His Thr
            35                  40                  45

Cys Lys Pro Met Ser Glu
            50
```

(2) INFORMATION FOR SEQ ID NO:4:

(i) SEQUENCE CHARACTERISTICS:
        (A) LENGTH: 30 amino acids
        (B) TYPE: amino acid
        (C) STRANDEDNESS: single
        (D) TOPOLOGY: linear    (ii) MOLECULE TYPE: peptide   (iii) HYPOTHETICAL: NO    (iv) ANTI-SENSE: NO     (v) FRAGMENT TYPE: N-terminal    (vi) ORIGINAL SOURCE:
       (A) ORGANISM: Barley Germin    (xi) SEQUENCE DESCRIPTION: SEQ ID NO:4:

```
Ser Asp Pro Asp Pro Leu Gln Asp Phe Cys Val Ala Asp Leu Asp Gly
 1               5                  10                  15

Lys Ala Val Ser Val Asn Gly His Thr Cys Lys Pro Met Ser
            20                  25                  30
```